(12) United States Patent
Chen et al.

(10) Patent No.: US 8,569,021 B2
(45) Date of Patent: Oct. 29, 2013

(54) MATERIALS AND METHODS FOR THE PRODUCTION OF BIODIESEL

(75) Inventors: Feng Chen, Knoxville, TN (US); Nan Zhao, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 254 days.

(21) Appl. No.: 12/967,233

(22) Filed: Dec. 14, 2010

(65) Prior Publication Data
US 2011/0167523 A1    Jul. 7, 2011

Related U.S. Application Data

(60) Provisional application No. 61/286,128, filed on Dec. 14, 2009.

(51) Int. Cl.
| C12P 7/62 | (2006.01) |
| C12P 7/64 | (2006.01) |
| C12P 1/04 | (2006.01) |
| C12N 1/19 | (2006.01) |
| C12N 1/20 | (2006.01) |
| C12N 1/21 | (2006.01) |
| C12N 15/29 | (2006.01) |
| C12N 15/54 | (2006.01) |

(52) U.S. Cl.
USPC ... 435/135; 435/134; 435/252.3; 435/252.31; 435/193; 435/257.2; 435/252.32; 435/252.33; 435/252.34; 435/252.35; 435/254.2; 536/23.6

(58) Field of Classification Search
None
See application file for complete search history.

(56) References Cited

U.S. PATENT DOCUMENTS

2010/0205696 A1 *   8/2010   Chen et al. ............... 800/300

OTHER PUBLICATIONS

Eggenberger et al 1949 Journal of Organic Chemistry 14:6 p. 1108-1110.*

* cited by examiner

*Primary Examiner* — David T Fox
*Assistant Examiner* — Matthew Keogh
(74) *Attorney, Agent, or Firm* — Saliwanchik, Lloyd & Eisenschenk

(57) ABSTRACT

The subject invention provides novel microorganisms comprising polynucleotides and polypeptides encoding a methyltransferase. The subject invention provides novel methods for the production of biodiesel.

13 Claims, 3 Drawing Sheets

1. Octanoic acid methyl ester
2. Nonanoic acid methyl ester
3. Decanoic acid methyl ester
4. Palmitic acid methyl ester MEVMQVLHMNKGDDENSYAKNSKVQSKIISLGKRINE
EAIMQMLCSNIPDIMGIADLGCSSGPNSLSVISEITD
IIYAKCRELGRPTPELKVFLNDLPHNDFNFIFGSLPA
FYDKLKKEKGSDFGPCFVSATPGSFYGRLFPSRSLHC
VHSSSSLHWLSQVPAGLESNARTAMNKGKIYISKSSS
LCVLEAYSLQFQKDFSSFLKSRSKEIVPGGCMLLSFM
GRRSTDPTTDESCYHWELLAQALMSMVSEGLVEKEKV
DSFNAPYYGPCVEEMRLEIEKDGSFSVNRLETFEIDW
DGGVDDVDTTSGAALRGQRVAKTIRAVVESMLESHFG
KDIMDELFRRYGEMVEGYLSKTGTKYTILVISMVRN

Fig. 2

MATERIALS AND METHODS FOR THE PRODUCTION OF BIODIESEL

CROSS-REFERENCE TO RELATED APPLICATION

This application claims the benefit of U.S. Provisional Patent Application 61/286,128, filed Dec. 14, 2009, the disclosure of which is hereby incorporated by reference in its entirety.

BACKGROUND OF THE INVENTION

Biodiesel has physico-chemical properties that are similar to those of petroleum-based diesel. Because of its renewability, biodiesel has attracted tremendous amount of interests from oil and chemical companies as well as newly emerged alternative fuel companies. The conventional process used for biodiesel production is cost intensive, which is partly attributed to the transesterification reaction (Bautista et al., 2009). In addition, despite numerous environmental benefits compared with petroleum-based diesel, the conventional biodiesel production also has some environmental challenges. For example, methanol, which is routinely used in the transesterification reaction, can be hazardous. When removing residual triglycerides and glycerol from the biodiesel product, multiple steps of water wash produce massive industrial wastewater that can have tremendous negative impact on the environment. Therefore, novel strategies for biodiesel production are highly sought by the industry.

Biodiesel is a mixture of fatty acid methyl esters (FAMEs) that are derived from a variety of crop oils, animal fats or waste oils. In the conventional process of biodiesel production, transesterification is a critical step. It utilizes basic or acid catalysts to convert triglycerides into FAMEs in the presence of methanol with glycerol as a byproduct. The existence of glycerol has been proved to affect the quality of biodiesel, such as viscosity, flash point and oxidation stability (Tan et al., 2010). Therefore, glycerol has to be removed.

In energy crops for biodiesel production, fatty acids are synthesized then condensed with glycerol to form triglycerides. This industrial practice has also led to the excessive supply of glycerol and its devaluation in the market price (Lu et al., 2008). The transesterification reaction itself also has a number of technical challenges, such as the low reaction rate when using the acid catalyst and the formation of soap in basic-based process. There have been numerous attempts focusing on improving the conventional transesterification process for biodiesel production. For example, several studies reported utilizing lipase as a catalyst to catalyze the removal of glycerol and the formation of FAMEs (Sanchez and Vasudevan, 2006). In a recent report, methyl acetate, instead of methanol, was used in the transesterification reaction in order to reduce the influence of glycerol (Tan et al., 2010). While some progress has been made in improvement of biodiesel production, break-though concepts and technologies still need to be developed in order to significantly lower the cost of biodiesel production to make it economically feasible.

BRIEF SUMMARY OF THE INVENTION

The subject invention provides microorganisms and methods for the production of biodiesel or biofuels. In various aspects of the invention, recombinant microorganisms expressing PtJBMT3 (SEQ ID NO: 2 or variants thereof) are contacted with crop oils, animal fats or waste oils and fatty acids within these materials are methylated by PtJBMT3 (or a variant thereof).

BRIEF DESCRIPTION OF THE SEQUENCES

SEQ ID NO:1 is the nucleic acid sequence that encodes the methyltransferase PtJBMT3.
SEQ ID NO:2 is the translated protein sequence encoded by SEQ ID NO:1.

BRIEF DESCRIPTION OF THE TABLES

Table 1: Amino acid substitution table.
Table 2: Exemplary fatty acids suitable for methylation by PtJBMTm3.

BRIEF DESCRIPTION OF THE FIGURES

FIG. 2: Sequence of PtJBMTm3 (SEQ ID NO: 2). Active site residues are in bold and double underlined.

DETAILED DESCRIPTION OF THE INVENTION

Figure 1:
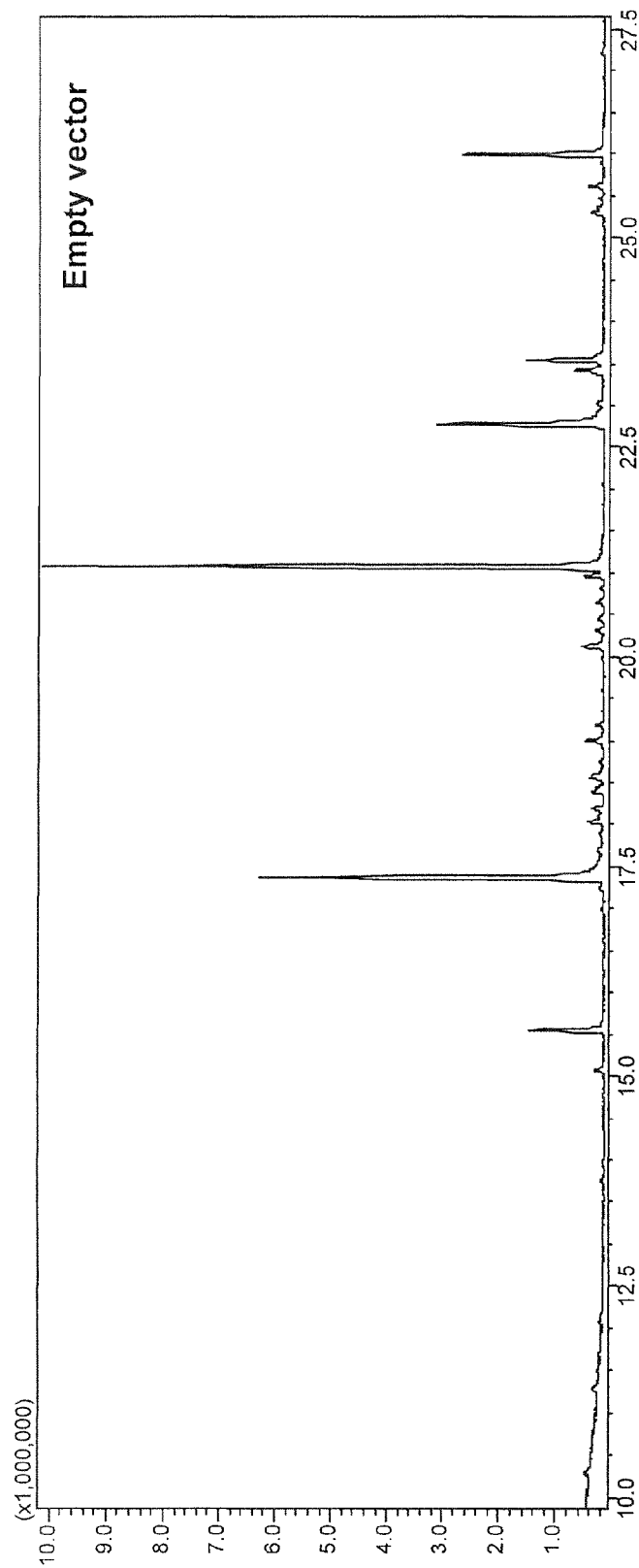
FIG. 1: Illustrates the production of methylated fatty acids by E. coli expressing PtJBMT3. In the E. coli system, recombinant PtJBMTm3 was shown to catalyze the formation of several FAMEs, such as octanoic acid methyl ester, decanoic acid methyl ester, and palmitic acid methyl ester.
Figure 1:
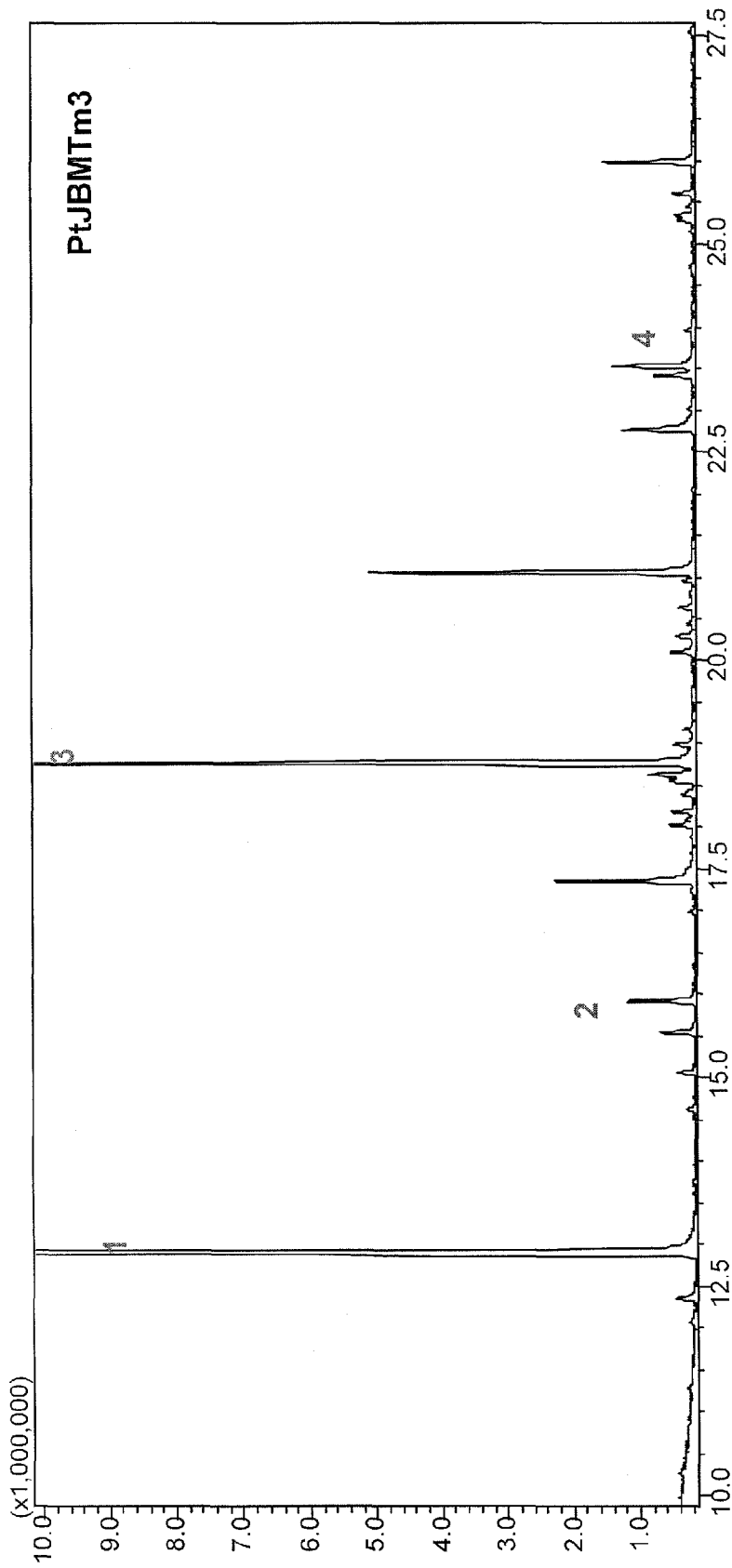

The development of a microorganism capable of methylating fatty acids found in a variety sources, such as crop oils, animal fats or waste oils would provide a valuable tool for the production of biodiesel or biofuels. As noted above, in the conventional process of biodiesel production, transesterification is a critical step and utilizes basic or acid catalysts to convert triglycerides into FAMEs in the presence of methanol with glycerol as a byproduct. The conventional process used for biodiesel production is cost intensive, which is partly attributed to the transesterification reaction and has environmental challenges. For example, methanol, which is routinely used in the transesterification reaction, can be hazardous and removing residual triglycerides and glycerol from the biodiesel product can produce massive industrial wastewater that can have tremendous negative impact on the environment.

Accordingly, one aspect of the subject invention provides microorganisms and methods for the production of biofuels (biodiesel) that can reduce the cost and environmental impact of biodiesel production. A novel gene (PtJBMTm3) has been identified which, when expressed in microorganisms, allows for the conversion of fatty acid containing materials into biodiesel or biofuel. PtJBMTm3 encodes a methyltransferase capable of methylating various fatty acids within various materials.

Nucleic Acids and Polypeptides

As discussed above, the subject invention provides microorganisms comprising nucleic acids and polypeptides designated as PtJBMTm3 (SEQ ID NO: 1) and PtJBMTm3 (SEQ ID NO: 2), respectively. PtJBMTm3 has the ability to methylate various fatty acids.

Accordingly, one aspect of the invention provides a microorganism expressing a polypeptide comprising SEQ ID NO: 2 (PtJBMTm3) or a variant thereof. Another aspect of the invention provides microorganisms expressing polypeptide fragments of SEQ ID NO: 2 (or variants thereof), wherein said fragments and variants have the ability to methylate fatty acids.

Polypeptide fragments according to the subject invention, usually comprise a contiguous span of at least 3, 4, 5, 6, 7, 8, 9, 10, 11, 12, 13, 14, 15, 16, 17, 18, 19, 20, 21 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363 or 364 consecutive amino acids of SEQ ID NO:2. Certain embodiments provide fragments of SEQ ID NO: 2 in which amino acids are deleted from the C-terminus, N-terminus or both the C-terminus and N-terminus of the polypeptide, provided that active site residues are not deleted (see FIG. 2). Any fragment of SEQ ID NO: 2 disclosed herein retains the biological activity of methylating fatty acids.

A "variant polypeptide" (or polypeptide variant) is to be understood to designate polypeptides exhibiting, in relation to the natural polypeptide, certain modifications. These modifications can include a deletion, addition, or substitution of at least one amino acid, a truncation, an extension, a chimeric fusion, a mutation, or polypeptides exhibiting post-translational modifications. Among these homologous variant polypeptides, are those comprising amino acid sequences exhibiting between at least (or at least about) 20.00% to 99.99% (inclusive) identity to the full length polypeptide (SEQ ID NO: 2) are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant polypeptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. In a preferred embodiment, a variant or modified polypeptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to SEQ ID NO: 2. Typically, the percent identity is calculated with reference to the full-length, native, and/or naturally occurring polypeptide (e.g., SEQ ID NO: 2). In all instances, variant polypeptides retain at least one of the activities associated with the polypeptide set forth in SEQ ID NOs: 2, particularly the ability to methylate a fatty acid.

In some embodiments, variant polypeptides contain no amino acid substitutions in the active site residues identified in FIG. 2 and amino acid substitutions can be made in various other amino acids. In other embodiments, amino acid substitutions can be made in active site residues. In other embodiments, variants in which several, i.e. between 5 and 10, 1 and 5, 1 and 3, 1 and 2 or just 1 amino acid(s) are substituted, deleted or added in any combination are provided. Especially preferred are silent substitutions, additions and deletions, which do not alter the properties and activities of the protein (i.e., the ability to methylate a fatty acid). Examples of suitable amino acid substitutions are provided below. For example, amino acids within the groups provided below may be substituted for each other. Alternatively, conservative/synonymous amino acids may be substituted for a given amino acid as illustrated in Table 1. In all instances, variant polypeptides retain at least one of the activities associated with the polypeptide set forth in SEQ ID NOs: 2, particularly the ability to methylate a fatty acid. Any amino acid substitution should be a "conservative", "synonymous" or "safe" substitution, which is commonly defined a substitution introducing an amino acids having sufficiently similar chemical properties (e.g. a basic, positively charged amino acid should be replaced by another basic, positively charged amino acid), in order to preserve the structure and the biological function of the molecule. Examples of such "conservative", "synonymous" or "safe" substitutions are provided in Table 1 and the literature provides many models on which the selection of conservative amino acids substitutions can be performed on the basis of statistical and physico-chemical studies on the sequence and/or the structure of proteins (Rogov S. I. and Nekrasov A. N., 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L. R. et al., 2000). The groups of synonymous and preferred synonymous amino acids are shown in Table 1. Alternatively, the application provides embodiments in which amino acids residues within each of the following groups can be substituted for each other: (i) Ala, Val, Leu and Ile; (ii) Ser and Thr; (iii) Asp and Glu; (iv) Asn and Gln; (v) Lys and Arg; or (vi) Phe and Tyr. In all instances, variant polypeptides retain at least one of the activities associated with the polypeptide set forth in SEQ ID NO: 2, particularly the ability to methylate a fatty acid. Yet another aspect of the invention provides a microorganism comprising:

a) a polynucleotide sequence encoding a polypeptide comprising SEQ ID NO: 2 or encoding one or a polynucleotide encoding a polypeptide fragment of SEQ ID NO: 2;

b) a polynucleotide sequence that is at least 70% identical to SEQ ID NO: 1 and encodes a polypeptide having methyltransferase activity or a polynucleotide that comprises SEQ ID NO: 1;

c) a polynucleotide sequence at least 8 consecutive nucleotides of a polynucleotide sequence as set forth in (a) or (b);

d) a polynucleotide that is complementary to the polynucleotides set forth in (a), (b) or (c);

e) a polynucleotide that hybridizes under low, intermediate or high stringency with a polynucleotide sequence as set forth in (a), (b), (c) or (d);

f) a genetic construct comprising a polynucleotide sequence as set forth in (a), (b), (c), (d) or (e); or g) a vector comprising a polynucleotide or genetic construct as set forth in (a), (b), (c), (d), (e) or (f);

Genetic constructs of the subject invention can also contain additional regulatory elements such as promoters and enhancers and, optionally, selectable markers. Also within the scope of the subject instant invention are vectors or expression cassettes containing genetic constructs as set forth herein or polynucleotides encoding the polypeptides, set forth supra, operably linked to regulatory elements (e.g., promoters or enhancers). The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include in the 5'-3' direction of transcription, a transcriptional and translational initiation region, a DNA sequence of the invention, and transcriptional and translational termination regions. The transcriptional initiation region, the promoter, may be native (analogous) or foreign (heterologous) to the host cell. Additionally, the promoter may be the natural sequence or alternatively a synthetic sequence. By "foreign" is intended that the transcriptional initiation region/promoter is not found in the native plant into which the transcriptional initiation region is introduced. As used herein, a chimeric gene comprises a coding sequence operably linked to a transcriptional initiation region that is heterologous to the coding sequence.

Another aspect of the invention provides vectors for the cloning and/or the expression of a polynucleotide sequence taught herein. Vectors of this invention can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide or peptide fragment encoded by a polynucleotide sequence disclosed herein comprising the culture of a host cell transformed with a polynucleotide of the subject invention under conditions that allow for the expression of the polypeptide and, optionally, recovering the expressed polypeptide. The host cell/microorganism, as disclosed herein, may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277, 375, 5,643,570, or 5,565,335, each of which is incorporated by reference in its entirety, including all references cited within each respective patent. Host cells/microorganisms can be selected from *Escherichia coli, Gluconobacter oxydans, Gluconobacter Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri, Sacchromyces* spp. or algae. In certain embodiments, the genetically modified host cell is an *E. coli*, yeast or algae. Non limiting examples of algae that can be used in this aspect of the invention include: *Botryococcus braunii; Neochloris oleoabundans; Scenedesmus dimorphus; Euglena gracilis; Nannochloropsis salina; Dunaliella tertiolecta; Tetraselmis chui; Isochrysis galbana; Phaeodactylum tricornutum; Pleurochrysis carterae; Prymnesium parvum; Tetraselmis suecica;* or *Spirulina* species. In various aspects of the invention, the cells are metabolically evolved. The terms "metabolically evolved" or "metabolic evolution" related to growth-based selection (metabolic evolution) of host cells that demonstrate improved growth (cell yield) and the production of methylated fatty acids.

Furthermore, a host cell may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in plant cells can be used to ensure "native" glycosylation of a plant-derived protein. Furthermore, different vector/host expression systems may effect processing reactions to different extents.

Still another aspect of the invention provides for transgenic oil crop plants. In this aspect of the invention, oil crop plants, such as oil palm, olive, coconut, peanut, soybean, cotton (cottonseed), sunflower (sunflowerseed), flax (flaxseed), corn, linseed, rapeseed, quinoa, canola or jartropha, are transformed with a nucleic acid encoding PtJBMTm3, fragments of PtJBMTm3, variants of PtJBMTm3 or fragments of said variants. As discussed above, fragments and variants of PtJBMTm3 retain the ability to methylate fatty acids.

The present invention is not limited to any particular method for transforming plant cells. Technology for introducing DNA into plant cells is well-known to those of skill in the art. Four basic methods for delivering foreign DNA into plant cells have been described. Chemical methods (Graham and van der Eb, 1973; Zatloukal et al., 1992); physical methods including microinjection (Capecchi, 1980), electroporation (Wong and Neumann 1982; Fromm et al., 1985; U.S. Pat. No. 5,384,253) and the gene gun (Johnston and Tang, 1994; Fynan et al., 1993); viral methods (Clapp, 1993; Lu et al., 1993; Eglitis and Anderson 1988; Eglitis et al., 1988); and receptor-mediated methods (Curiel et al., 1991; Curiel et al., 1992; Wagner et al., 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material with pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al, (1985) and Rogers et al. (1987). Further, the integration of the Ti-DNA is a relatively precise process resulting in few rearrangements. The region of DNA to be transferred is defined by the border sequences, and intervening DNA is usually inserted into the plant genome as described in Spielmann et al. (1986) and Jorgensen et al. (1987).

*Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985; Marcotte et al., 1988). Application of these systems to different plant species depends on the ability to regenerate the particular species from protoplasts.

The introduction of nucleic acids encoding PtJBMTm3 into an oil crop plant or an oil crop plant cell, and its subsequent expression, provides for the ability to produce biodiesel within the oil crop plant or cell. Plants producing PtJBMTm3 proteins will preferably produce sufficient amounts of protein that will render the plant a photosynthetic biodiesel production platform.

Plant cells transfected with a PtJBMTm3 encoding polynucleotide (or a fatty acid methylating fragment or variant thereof) can be regenerated into whole plants. The subject invention includes cell cultures including tissue cell cultures, liquid cultures, and plated cultures. Seeds produced by and/or used to generate plants of the subject invention are also included within the scope of the subject invention. Other plant tissues and parts are also included in the subject invention. The subject invention likewise includes methods of producing plants or cells comprising a polynucleotide of the subject invention. One preferred method of producing such plants is by planting a seed of the subject invention.

Another aspect of the invention provides methods of making biofuels or biodiesel. In this aspect of the invention, host cells or microorganisms expressing PtJBMTm3, or fragments or variants thereof, are contacted with a source containing fatty acids. As noted above, various materials comprising fatty acids are know to those skilled in the art. Non-limiting examples of such materials include crop oils, animal fats or waste oils. Non-limiting examples of crop oils include: sunflower oil, rapeseed oil, thistle oil, soybean oil, linseed oil, peanut oil, tallows, olive oil, castor oil, palm oil, palm oil fractions, such as palm olein and palm stearin, yatropha oil, coconut oil and/or palm kernel oil.

As discussed above, PtJBMT3 (and variants or fragments thereof) have the ability to methylate fatty acids found within crop oils, animal fats or waste oils. Thus, another aspect of the invention provides methods of methylating a fatty acid comprising culturing a host cell/microorganism in a medium comprising a fatty acid under conditions that allow for the methylation of one or more fatty acid within the medium. As noted above, fatty acids that may be methylated, as described herein include: octanoic, nonanoic, decanoic, hexadecanoic acid and/or those identified in Table 2. Additional examples of fatty acids, obtainable from vegetable oils, that are suitable for methylation include, and are not limited to, lauroleic, myristoleic, palmitoleic, petroselaidic, oleic, elaidic, ricinoleic, linoleic, linolaidic, linolenic, gadoleic, arachidonic and erucic acid esters. Mixtures of the methyl and/or ethyl esters of these acids are also suitable.

TABLE 1

Amino Acid Substitution Table

| Amino Acid | Conservative/Synonymous Amino Acids | Preferred Conservative/Synonymous Amino Acids |
|---|---|---|
| Ser | Gly, Ala, Ser, Thr, Pro | Thr, Ser |
| Arg | Asn, Lys, Gln, Arg, His | Arg, Lys, His |

TABLE 1-continued

Amino Acid Substitution Table

| Amino Acid | Conservative/Synonymous Amino Acids | Preferred Conservative/Synonymous Amino Acids |
|---|---|---|
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn. Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE 2

Fatty Acids

| | |
|---|---|
| Saturated | Acetic (C2) • Propionic (C3) • Butyric (C4) • Valeric (C5) • Hexanoic (C6) • Heptanoic (C7) • Caprylic (C8) • Nonanoic (C9) • Capric (C10) • Lauric (C12) • Myristic (C14) • Palmitic (C16) • Heptadecanoic (C17) • Stearic (C18) • Arachidic (C20) • Behenic (C22) • Lignoceric (C24) |
| n-3 Unsaturated | α-Linolenic • Stearidonic • Eicosapentaenoic • Docosahexaenoic |
| n-6 Unsaturated | Linoleic • γ-Linolenic • Dihomo-γ-linolenic • Arachidonic |
| n-9 Unsaturated | Oleic • Elaidic • Eicosenoic • Erucic • Nervonic |

We claim:

1. A composition comprising: a genetically modified microorganism comprising a nucleic acid encoding SEQ ID NO: 2 operably linked to a promoter, and a culture medium comprising $C_2$ to $C_{10}$ fatty acids.

2. The composition of claim 1, wherein said genetically modified microorganism is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri,* or *Xanthomonas citri.*

3. The composition of claim 2, wherein said genetically modified microorganism is *Escherichia coli.*

4. The composition of claim 1, wherein said genetically modified microorganism is a yeast.

5. The composition of claim 1, wherein said genetically modified microorganism is an alga.

6. A method of producing methylated fatty acids comprising: culturing one or more genetically modified microorganism comprising a nucleic acid encoding SEQ ID NO: 2 operably linked to a promoter, in a culture medium comprising $C_2$ to $C_{10}$ fatty acids under conditions that allow for the methylation of said $C_2$ to $C_{10}$ fatty acids.

7. A method of making a biodiesel comprising: culturing a genetically modified microorganism comprising a nucleic acid encoding SEQ ID NO: 2 operably linked to a promoter, in a medium comprising: a crop oil, waste oil or animal fat; and methylating fatty acids in said medium, said fatty acids being: Acetic (C2) acid, Propionic (C3) acid, Butyric (C4) acid, Valeric (C5) acid, Hexanoic (C6) acid, Heptanoic (C7) acid, Caprylic (C8) acid, Nonanoic (C9) acid, or Capric (C10) acid.

8. The method of claim 7, wherein said fatty acid is caprylic acid, nonanoic acid, or capric acid.

9. The method of claim 7, wherein said crop oil is one or more crop oil selected from the group consisting of sunflower oil, rapeseed oil, thistle oil, soybean oil, linseed oil, peanut oil, tallows, olive oil, castor oil, palm oil, palm oil fractions, yatropha oil, coconut oil and palm kernel oil.

10. A composition comprising: culture medium and a genetically modified microorganism comprising a nucleic acid encoding SEQ ID NO: 2 operably linked to a promoter, said culture medium comprising a crop oil, animal fats or waste oils, said crop oil, animal fats or waste oils containing $C_2$ to $C_{10}$ fatty acids.

11. The composition of claim 10, wherein said crop oil is sunflower oil, rapeseed oil, thistle oil, soybean oil, linseed oil, peanut oil, tallows, olive oil, castor oil, palm oil, palm oil fractions, yatropha oil, coconut oil or palm kernel oil.

12. The method of claim 9, wherein said palm oil fractions are palm olein or palm stearin.

13. The composition of claim 11, wherein said palm oil fractions are palm olein or palm stearin.

* * * * *

SEQUENCE LISTING

```
<160> NUMBER OF SEQ ID NOS: 2

<210> SEQ ID NO 1
<211> LENGTH: 1110
<212> TYPE: DNA
<213> ORGANISM: poplar trees
<220> FEATURE:
<221> NAME/KEY: CDS
<222> LOCATION: (1)..(1110)

<400> SEQUENCE: 1 atg gaa gta atg caa gtg ctt cac atg aac aaa gga gat gat gaa aat       48
Met Glu Val Met Gln Val Leu His Met Asn Lys Gly Asp Asp Glu Asn
1               5                   10                  15 agt tat gca aaa aac tcg aaa gtg cag agc aag ata ata tct cta gga       96
Ser Tyr Ala Lys Asn Ser Lys Val Gln Ser Lys Ile Ile Ser Leu Gly
            20                  25                  30 aag cga atc aat gag gag gct ata atg caa atg ttg tgc agc aat atc      144
Lys Arg Ile Asn Glu Glu Ala Ile Met Gln Met Leu Cys Ser Asn Ile
        35                  40                  45 cct gac atc atg ggt att gca gac ctg ggt tgc tcc tct gga cct aac      192
Pro Asp Ile Met Gly Ile Ala Asp Leu Gly Cys Ser Ser Gly Pro Asn
```

-continued

```
            50                  55                  60
tcg ttg tca gtg atc tcc gaa att act gat atc atc tat gcc aaa tgc      240
Ser Leu Ser Val Ile Ser Glu Ile Thr Asp Ile Ile Tyr Ala Lys Cys
 65                  70                  75                  80 aga gag ttg ggg cgt cca aca cca gaa ctt aag gtc ttc ctg aat gat      288
Arg Glu Leu Gly Arg Pro Thr Pro Glu Leu Lys Val Phe Leu Asn Asp
                 85                  90                  95 ctt cct cat aat gac ttc aat ttt att ttt gga tcc ttg cca gca ttc      336
Leu Pro His Asn Asp Phe Asn Phe Ile Phe Gly Ser Leu Pro Ala Phe
            100                 105                 110 tat gat aaa tta aag aaa gaa aag ggt tcc gac ttc ggg cca tgc ttt      384
Tyr Asp Lys Leu Lys Lys Glu Lys Gly Ser Asp Phe Gly Pro Cys Phe
                115                 120                 125 gta tca gca acg ccg ggt tct ttc tat ggt aga ttg ttt cct agc agg      432
Val Ser Ala Thr Pro Gly Ser Phe Tyr Gly Arg Leu Phe Pro Ser Arg
            130                 135                 140 agc ttg cat tgt gtg cac tct tct tct agt ctt cac tgg ctc tcg cag      480
Ser Leu His Cys Val His Ser Ser Ser Ser Leu His Trp Leu Ser Gln
145                 150                 155                 160 gtt cca gct ggt cta gag agc aac gcg agg acg gcc atg aac aag gga      528
Val Pro Ala Gly Leu Glu Ser Asn Ala Arg Thr Ala Met Asn Lys Gly
                165                 170                 175 aag att tat ata tca aag tca agc tcg ctt tgt gtg tta gaa gca tat      576
Lys Ile Tyr Ile Ser Lys Ser Ser Ser Leu Cys Val Leu Glu Ala Tyr
            180                 185                 190 tca ttg cag ttt caa aaa gac ttt tcg tcg ttt cta aaa tca cgt tcg      624
Ser Leu Gln Phe Gln Lys Asp Phe Ser Ser Phe Leu Lys Ser Arg Ser
                195                 200                 205 aag gaa att gtt ccc gga ggc tgc atg ctc ttg tca ttc atg ggc agg      672
Lys Glu Ile Val Pro Gly Gly Cys Met Leu Leu Ser Phe Met Gly Arg
            210                 215                 220 aga tct acc gat ccc acc acg gac gag agt tgc tac cat tgg gag ctc      720
Arg Ser Thr Asp Pro Thr Thr Asp Glu Ser Cys Tyr His Trp Glu Leu
225                 230                 235                 240 tta gca cag gca cta atg agc atg gtt tct gag ggg ctc gtc gag aaa      768
Leu Ala Gln Ala Leu Met Ser Met Val Ser Glu Gly Leu Val Glu Lys
                245                 250                 255 gaa aag gtc gat tcc ttt aac gcc ccc tac tat ggt cca tgt gtg gaa      816
Glu Lys Val Asp Ser Phe Asn Ala Pro Tyr Tyr Gly Pro Cys Val Glu
            260                 265                 270 gaa atg agg tta gag att gaa aag gat ggt tct ttc agt gtc aat cgg      864
Glu Met Arg Leu Glu Ile Glu Lys Asp Gly Ser Phe Ser Val Asn Arg
                275                 280                 285 ctc gag acc ttt gaa att gac tgg gat gga ggt gtc gac gat gtg gac      912
Leu Glu Thr Phe Glu Ile Asp Trp Asp Gly Gly Val Asp Asp Val Asp
            290                 295                 300 acc acg tct ggg gca gca tta cgt gga cag aga gtg gcc aag aca atc      960
Thr Thr Ser Gly Ala Ala Leu Arg Gly Gln Arg Val Ala Lys Thr Ile
305                 310                 315                 320 aga gct gtc gtg gag tcg atg ctg gaa tct cat ttt ggg aag gac ata     1008
Arg Ala Val Val Glu Ser Met Leu Glu Ser His Phe Gly Lys Asp Ile
                325                 330                 335 atg gac gaa tta ttt cga agg tat gga gag atg gtg gag ggt tac ttg     1056
Met Asp Glu Leu Phe Arg Arg Tyr Gly Glu Met Val Glu Gly Tyr Leu
            340                 345                 350 tca aag acc gga acc aag tac acc atc ttg gtc att tca atg gtt aga     1104
Ser Lys Thr Gly Thr Lys Tyr Thr Ile Leu Val Ile Ser Met Val Arg
                355                 360                 365 aat taa                                                              1110
Asn
```

<210> SEQ ID NO 2
<211> LENGTH: 369
<212> TYPE: PRT
<213> ORGANISM: poplar trees

<400> SEQUENCE: 2

Met Glu Val Met Gln Val Leu His Met Asn Lys Gly Asp Asp Glu Asn
1               5                   10                  15

Ser Tyr Ala Lys Asn Ser Lys Val Gln Ser Lys Ile Ile Ser Leu Gly
            20                  25                  30

Lys Arg Ile Asn Glu Glu Ala Ile Met Gln Met Leu Cys Ser Asn Ile
        35                  40                  45

Pro Asp Ile Met Gly Ile Ala Asp Leu Gly Cys Ser Ser Gly Pro Asn
    50                  55                  60

Ser Leu Ser Val Ile Ser Glu Ile Thr Asp Ile Ile Tyr Ala Lys Cys
65                  70                  75                  80

Arg Glu Leu Gly Arg Pro Thr Pro Glu Leu Lys Val Phe Leu Asn Asp
                85                  90                  95

Leu Pro His Asn Asp Phe Asn Phe Ile Phe Gly Ser Leu Pro Ala Phe
            100                 105                 110

Tyr Asp Lys Leu Lys Lys Glu Lys Gly Ser Asp Phe Gly Pro Cys Phe
        115                 120                 125

Val Ser Ala Thr Pro Gly Ser Phe Tyr Gly Arg Leu Phe Pro Ser Arg
    130                 135                 140

Ser Leu His Cys Val His Ser Ser Ser Leu His Trp Leu Ser Gln
145                 150                 155                 160

Val Pro Ala Gly Leu Glu Ser Asn Ala Arg Thr Ala Met Asn Lys Gly
                165                 170                 175

Lys Ile Tyr Ile Ser Lys Ser Ser Leu Cys Val Leu Glu Ala Tyr
            180                 185                 190

Ser Leu Gln Phe Gln Lys Asp Phe Ser Ser Phe Leu Lys Ser Arg Ser
        195                 200                 205

Lys Glu Ile Val Pro Gly Gly Cys Met Leu Leu Ser Phe Met Gly Arg
    210                 215                 220

Arg Ser Thr Asp Pro Thr Thr Asp Glu Ser Cys Tyr His Trp Glu Leu
225                 230                 235                 240

Leu Ala Gln Ala Leu Met Ser Met Val Ser Glu Gly Leu Val Glu Lys
                245                 250                 255

Glu Lys Val Asp Ser Phe Asn Ala Pro Tyr Tyr Gly Pro Cys Val Glu
            260                 265                 270

Glu Met Arg Leu Glu Ile Glu Lys Asp Gly Ser Phe Ser Val Asn Arg
        275                 280                 285

Leu Glu Thr Phe Glu Ile Asp Trp Asp Gly Val Asp Asp Val Asp
    290                 295                 300

Thr Thr Ser Gly Ala Ala Leu Arg Gly Gln Arg Val Ala Lys Thr Ile
305                 310                 315                 320

Arg Ala Val Val Glu Ser Met Leu Glu Ser His Phe Gly Lys Asp Ile
                325                 330                 335

Met Asp Glu Leu Phe Arg Arg Tyr Gly Glu Met Val Glu Gly Tyr Leu
            340                 345                 350

Ser Lys Thr Gly Thr Lys Tyr Thr Ile Leu Val Ile Ser Met Val Arg
        355                 360                 365

Asn